(12) United States Patent
Malladi et al.

(10) Patent No.: US 6,326,498 B1
(45) Date of Patent: Dec. 4, 2001

(54) PROCESS FOR THE SYNTHESIS OF 5-(2-FLUROPHENYL)-1H-TETRAZOLE

(75) Inventors: Pardhasaradhi Malladi; Srinivas Kantevari; Chembumkulam Kamalakshyamma Snehalatha Nair, all of Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/804,990

(22) Filed: Mar. 13, 2001

(51) Int. Cl.⁷ .................................................. C07D 257/06
(52) U.S. Cl. ................................................................ 548/250
(58) Field of Search ............................................. 548/250

(56) References Cited

PUBLICATIONS

Russell et al, "Efficient synthesis of 5–, etc" CA 119:160199 (1993).*

* cited by examiner

Primary Examiner—Patricia L. Morris

(74) Attorney, Agent, or Firm—Ladas & Parry

(57) ABSTRACT

The present invention discloses a process of the preparation of 5-(2-flurophenyl)-1H-tetrazole of the formula 2 by reacting 2-fluoro benzonitrile of the formula 1

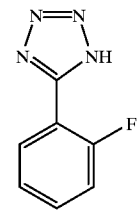

2

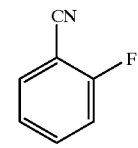

1 with an inorganic azide and an amine salt in an aromatic solvent, precipitating the product with hydrochloric acid and separating the precipitated product.

6 Claims, No Drawings

PROCESS FOR THE SYNTHESIS OF 5-(2-FLUROPHENYL)-1H-TETRAZOLE

FIELD OF THE INVENTION

The present invention relates to a process for the synthesis of 5-(2-flurophenyl)-1H-tetrazole.

BACKGROUND OF THE INVENTION

Tetrazole and its derivatives are used in the preparation of medicines, agricultural chemicals, foaming agents and automobile inflators. [J. Org. Prep. Proced. Int. 1994, 26, 499; CA 1995, 122, 31359r; Comprehensive Heterocyclic Chemistry II; Storr, R. C. Ed. Elsevier; Oxford, Uk, 1996, vol 4, p621–678].

The preparation of Losartan, a non-peptide angiotensin-II receptro antagonist requires the synthesis of 5-(4'-methyl[1,1'-biphenyl]-2-yl)-1H-tetrazole of the formula 3 below as an intermediate. Basically these approaches consist of the tetrazolyation of 2-cyano-4'-methyl biphenyl of the formula 4 below using tributyl tin azide. [J. Org. Chem. 1991, 36, 2395; U.S. Pat. No. 5,130,439].

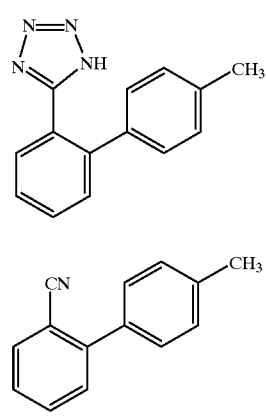

This approach has several drawbacks like longer reaction times and the usage of highly toxic trialkyl tin azide reagents. This process also requires a rigorous purification from stannous compounds in order to obtain the desired biphenyl tetrazole derivatives.

The second approach for the synthesis of biphenyl tetrazole of formula 3 involves the preparation of 5-phenyl-1H-tetrazole with a proper substituent at the ortho position of the phenyl ring such that the biphenyl linkage can be established subsequently. [J. Org. Chem. 1993, 38, 5023]. It has been observed that the ortho substituent suitable for the establishment of the biphenyl linkage is a fluorine atom. 5-(2-fluorophenyl)-1H-tetrazole can be reacted with p-toluene magnesium bromide via Grignard reaction to give 4'methyl 2'-(tetrazolyl)biphenyl in excellent purity. Under the same conditions 5-(2-chlorophenyl)-1H-tetrazole and 5-(2-bromophenyl)-1H-tetrazole failed to provide the desired biphenyl tetrazoles via Grignard reaction because of intramolecular chelation and steric hindrance.

Prior art available to the applicants discloses only one method for the preparation of 5-(2-fluorophenyl)-1H-tetrazole in 69.8% yield [J. Org. Chem. 1993, 38, 5023]. The disclosure in this reference involves the refluxing of 2-fluoro benzonitrile with sodium azide and acetic acid in butanol for two days. The practical utility of this method is suspect due to the in situ generation of hydrozoic acid, which is poisonous and also explosive.

It is therefore essential to develop an efficient method for the preparation of 5-(2-flurophenyl)-1H-tetrazole in order to achieve an efficient process for the preparation of angiotensin—II receptor antagonist Losartan avoiding the drawbacks of the prior art above.

OBJECTS OF THE INVENTION

It is an object of the invention to provide a process for the preparation of 5-(2-flurophenyl)-1H-tetrazole with improved efficiency.

It is an object of the invention to provide a process for the preparation of 5-(2-flurophenyl)-1H-tetrazole with improved yield.

It is an object of the invention to provide a process for the preparation of 5-(2-flurophenyl)-1H-tetrazole wherein the formation of poisonous material is avoided.

SUMMARY OF THE INVENTION

Accordingly the present invention provides a process of the preparation of 5-(2-flurophenyl)-1H-tetrazole of the formula 2

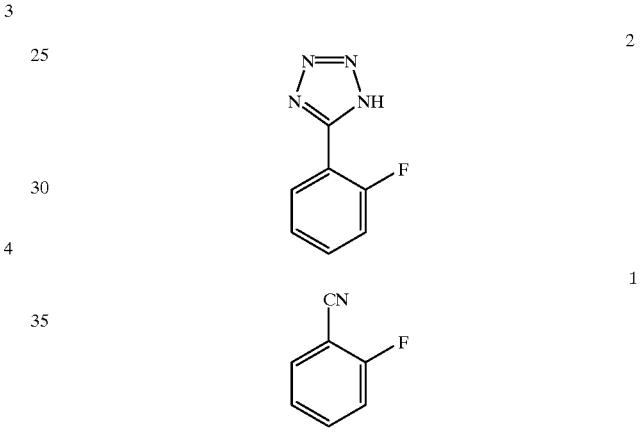

comprising reacting 2-fluoro benzonitrile of the formula 1 with with an inorganic azide and an amine salt in an aromatic solvent at a temperature in the range in of 80 to 150° C. for a time period in the range of 5 to 12 hours, cooling to room temperature, adding water to the reaction mixture, precipitating with hydrochloric acid, separating the precipitated product.

In one embodiment of the invention, the inorganic azide is sodium azide.

In another embodiment of the invention, the amine salt is triethyl ammonium chloride.

In yet another embodiment of the invention, the aromatic solvent is selected from the group consisting of toluene, benzene and xylene.

In a further embodiment of the invention, the time period ranges from 8 to 10 hours.

In a further embodiment of the invention, the reaction is conducted for a time period in the range of 8–10 hours.

DETAILED DESCRIPTION OF THE INVENTION

The process of the present invention is detailed below.

In the preparation of 5-(2-flurophenyl)-1H-tetrazole of the formula 2, a mixture of 2-fluorobenzonitrile of formula 1, sodium azide and triethyl ammonium hydrochloride and an aromatic solvent such as benzene, toluene or xylene are reacted at a temperature preferably in the range of 80 to 120° C. For a time period prefereably in the range of 6 to 10 hours. After cooling the product was extracted into water, concentrated HCl added to precipitate the 5-(2-flurophenyl)-1H-tetrazole of the formula 2, the resultant product filtered, dried and recrystallised from ethyl acetate and hexane.

The following examples are given by way of illustration and should not be construed as limiting the scope of the present invention.

EXAMPLE 1

Into a 250 ml round bottom flask equipped with a mechanical stirrer, thermometer and reflux condenser, 2-fluorobenzonitrile (17.0 g, 0.140 mol), sodium azide (12.48 g, 0.192 mol), triethyl ammonium hydrochloride (26.15 g, 0.193 mol), and toluene (175 ml) were taken. The mixture was heated to gentle reflux (98° C.) For 8 hours. After cooling the reaction mixture to room temperature, water (150 ml) was added to bring the triethyl amine salt of the product to the water layer and the neutral materials remained in the toluene layer. Concentrated HCl was added drop wise to the water layer at pH of 2 to precipitate out the product. The precipitate was filtered, washed with water, dried and weighed (22.8 g). Recrystallisation from ethyl acetate and hexane gave 21 g of the pure product in 91% yield. M.p. 146.5° C.

EXAMPLE 2

Into a 250 ml round bottom flask equipped with a mechanical stirrer, thermometer and reflux condenser, 2-fluorobenzonitrile (17.0 g, 0.140 mol), sodium azide (9.1 g, 0.140 mol), triethyl ammonium hydrochloride (19.27 g, 0.140 mol), and toluene (175 ml) were taken. The mixture was heated to gentle reflux (98° C.) for 8 hours. After cooling the reaction mixture to room temperature, water (150 ml) was added to bring the triethyl amine salt of the product to the water layer and the neutral materials remained in the toluene layer. Concentrated HCl was added drop wise to the water layer at pH of 2 to precipitate out the product. The precipitate was filtered, washed with water, dried and weighed (19 g). Recrystallisation from ethyl acetate and hexane gave 17.3 g of the pure product in 75% yield.

EXAMPLE 3

Into a 250 ml round bottom flask equipped with a mechanical stirrer, thermometer and reflux condenser, 2-fluorobenzonitrile (17.0 g, 0.140 mol), sodium azide (12.48 g, 0.192 mol), triethyl ammonium hydrochloride (26.15 g, 0.193 mol), and benzene (175 ml) were taken. The mixture was heated to gentle reflux (76–79° C.) For 8 hours. After cooling the reaction mixture to room temperature, water (150 ml) was added to bring the triethyl amine salt of the product to the water layer and the neutral materials remained in the toluene layer. Concentrated HCl was added drop wise to the water layer at pH of 2 to precipitate out the product. The precipitate was filtered, washed with water, dried and weighed (19 g). Recrystallisation from ethyl acetate and hexane gave 17 g of the pure product in 75% yield.

EXAMPLE 4

Into a 250 ml round bottom flask equipped with a mechanical stirrer, thermometer and reflux condenser, 2-fluorobenzonitrile (17.0 g, 0.140 mol), sodium azide (12.48 g, 0.192 mol), triethyl ammonium hydrochloride (26.15 g, 0.193 mol), and toluene (175 ml) were taken. The mixture was heated to gentle reflux (98° C.) For 8 hours. After cooling the reaction mixture to room temperature, water ( 150 ml) was added to bring the triethyl amine salt of the product to the water layer and the neutral materials remained in the toluene layer. Concentrated HCl was added drop wise to the water layer at pH of 2 to precipitate out the product. The precipitate was filtered, washed with water, dried and weighed (17 g). Recrystallisation from ethyl acetate and hexane gave 15 g of the pure product in 65% yield.

The main advantages of the invention are:
1. The preparation of 5-(2-flurophenyl)-1H-tetrazole in higher yield and greater purity as compared to prior art literature where sodium azide and acetic acid are used.
2. The production of poisonous and explosive hydrozoic acid is avoided.
3. Reaction takes place rapidly with no formation of byproducts.

We claim:
1. A process of the preparation of 5-(2-flurophenyl)-1H-tetrazole of the formula 2 comprising reacting 2-fluoro benzonitrile of the formula 1

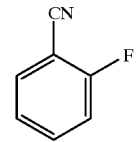

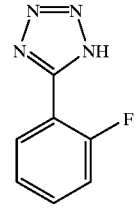

with an inorganic azide and an amine salt in an aromatic solvent at a temperature in the range in of 80 to 150° C. for a time period in the range of 5 to 12 hours, cooling to room temperature, adding water to the reaction mixture, precipitating with hydrochloric acid, separating the precipitated product.

2. A process as claimed in claim 1 wherein the inorganic azide is sodium azide.

3. A process as claimed in claim 1 wherein the the amine salt is triethyl ammonium chloride.

4. A process as claimed in claim 1 wherein the aromatic solvent is selected from the group consisting of toluene, benzene and xylene.

5. A process as claimed in claim 1 wherein the time period ranges from 8 to 10 hours.

6. A process as claimed in claim 1 wherein the reaction is conducted for a time period in the range of 8–10 hours.

* * * * *